United States Patent [19]
Schraga

[11] Patent Number: 5,468,233
[45] Date of Patent: Nov. 21, 1995

[54] HYPODERMIC DOSAGE MEASURING DEVICE

[76] Inventor: Steven Schraga, 1841 NE. 146 St., North Miami, Fla. 33181

[21] Appl. No.: 161,461

[22] Filed: Dec. 6, 1993

[51] Int. Cl.$^6$ .................................................. A61M 5/00
[52] U.S. Cl. ........................... 604/207; 604/407; 141/27; 141/94; 73/863.01
[58] Field of Search .................................. 604/207, 407; 73/863.01, 863.23, 863.24; 141/2, 18, 21, 22, 25–27, 94, 95, 311 R, 318, 319, 323, 328–330, 346, 353, 357, 358, 360, 362, 363, 369, 372–376, 391

[56] References Cited

U.S. PATENT DOCUMENTS

| | | | |
|---|---|---|---|
| 2,586,581 | 2/1952 | Tschischeck | 604/207 |
| 2,861,570 | 11/1958 | Beecher | 604/407 |
| 3,807,464 | 4/1974 | Pitesky | 141/375 |
| 3,833,030 | 9/1974 | Waldbauer, Jr. et al. | 141/26 |
| 3,875,979 | 4/1975 | Hults | 141/27 |
| 4,252,159 | 2/1981 | Maki | 141/95 |
| 4,274,453 | 6/1981 | Lee | 141/329 |
| 4,357,971 | 11/1982 | Friedman | 141/27 |
| 4,434,820 | 3/1984 | Glass | 141/2 |
| 4,475,915 | 10/1984 | Sloane | 141/27 |
| 4,489,766 | 12/1984 | Montada | 141/27 |
| 4,882,101 | 11/1989 | Strong | 604/407 |

FOREIGN PATENT DOCUMENTS

| | | | |
|---|---|---|---|
| 1026593 | 4/1966 | United Kingdom | 604/207 |
| 1179888 | 2/1970 | United Kingdom | 604/207 |

*Primary Examiner*—C. Fred Rosenbaum
*Assistant Examiner*—Ronald K. Stright, Jr.
*Attorney, Agent, or Firm*—Sandler Greenblum & Bernstein

[57] ABSTRACT

A hypodermic dosage measuring device to be utilized with a hypodermic syringe and a conventional drug vial, the dosage measuring device including a vial holding portion adapted to hold a head of the drug vial non-slidably therein, a syringe holding portion adapted to hold the syringe in a non-slidable position with a needle of the syringe disposed within the drug vial, and a dose adjustment portion, the dose adjustment portion including an elongate plunger holder and gear element, the plunger holder and gear element each including a plurality of teeth thereon such that movement of the gear element results in an elongate track segment of the plunger holder sliding in a longitudinal direction parallel to a length of the syringe. The plunger holder further including a plunger engagement segment extending perpendicularly from a proximal end of the track segment, the plunger engagement section being adapted to engage a plunger of the syringe such that longitudinal movement of the plunger holder results in corresponding longitudinal movement of the plunger of the syringe relative to a dosage holding area of the syringe, the precise dosage measure being indicated by dosage indicating indicia on the dose adjustment portion.

11 Claims, 3 Drawing Sheets

U.S. Patent     Nov. 21, 1995     Sheet 1 of 3     5,468,233
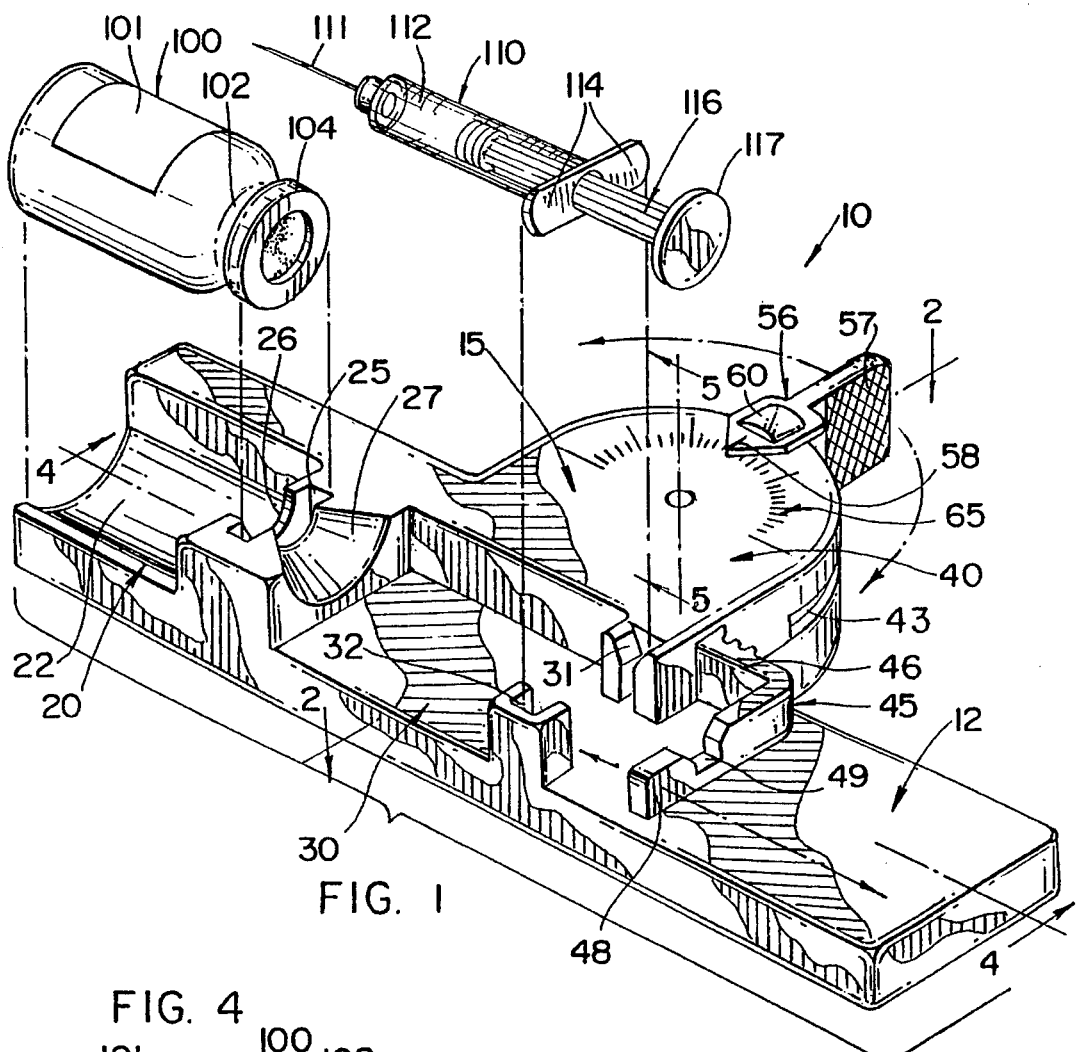
FIG. 1
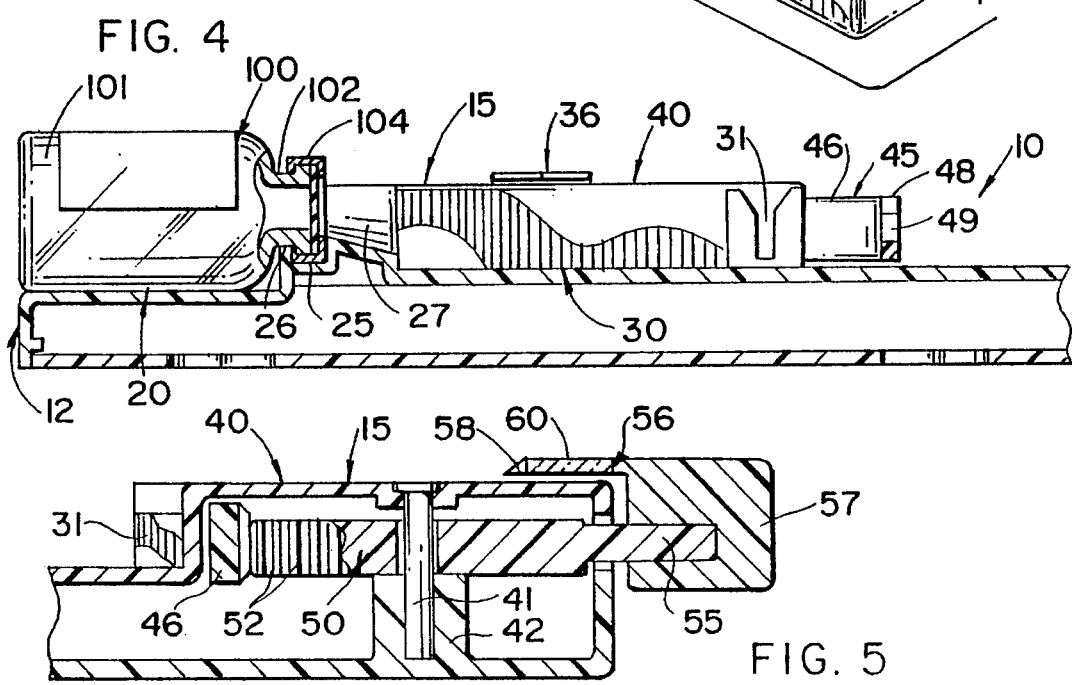
FIG. 4
FIG. 5

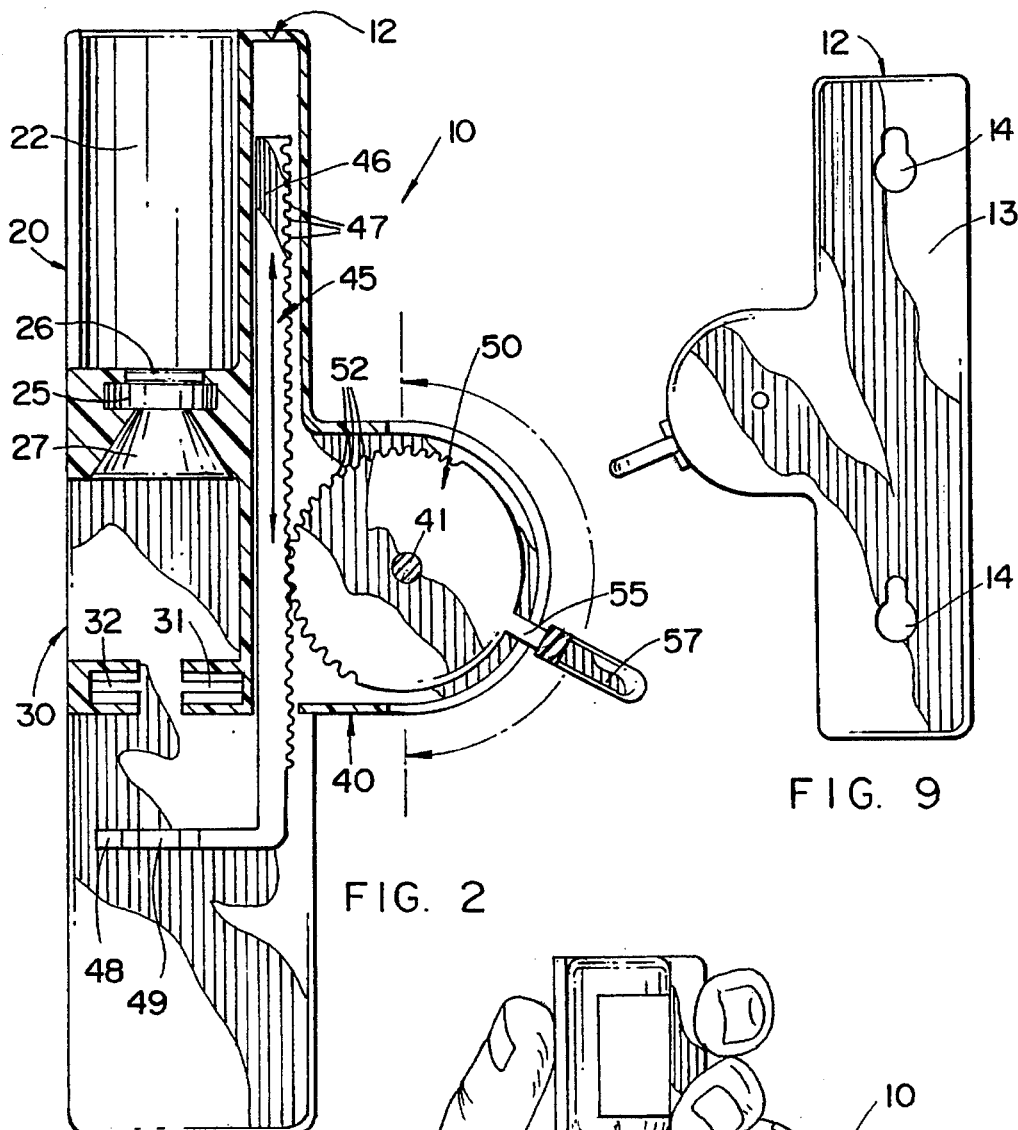
FIG. 2
FIG. 9
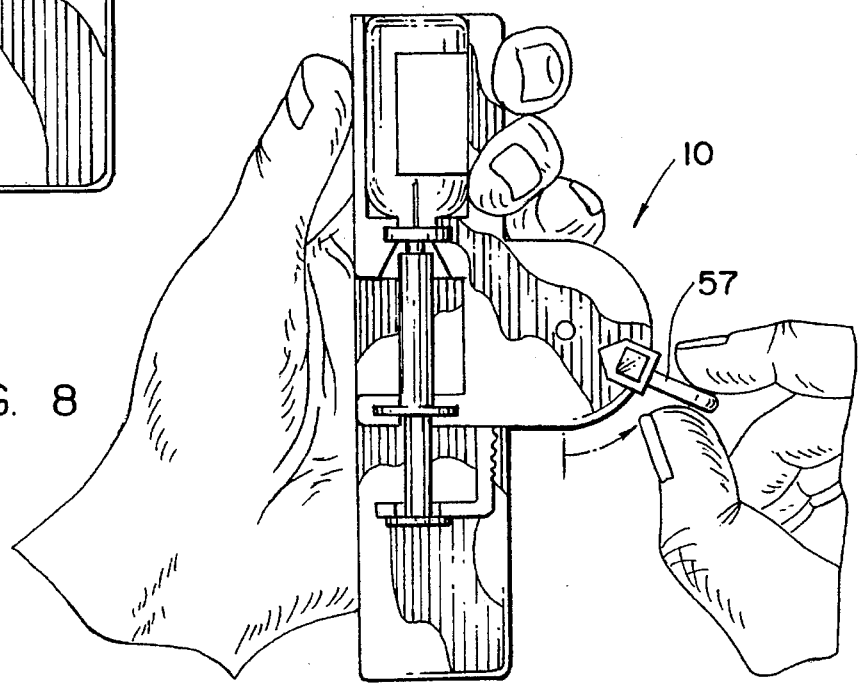
FIG. 8

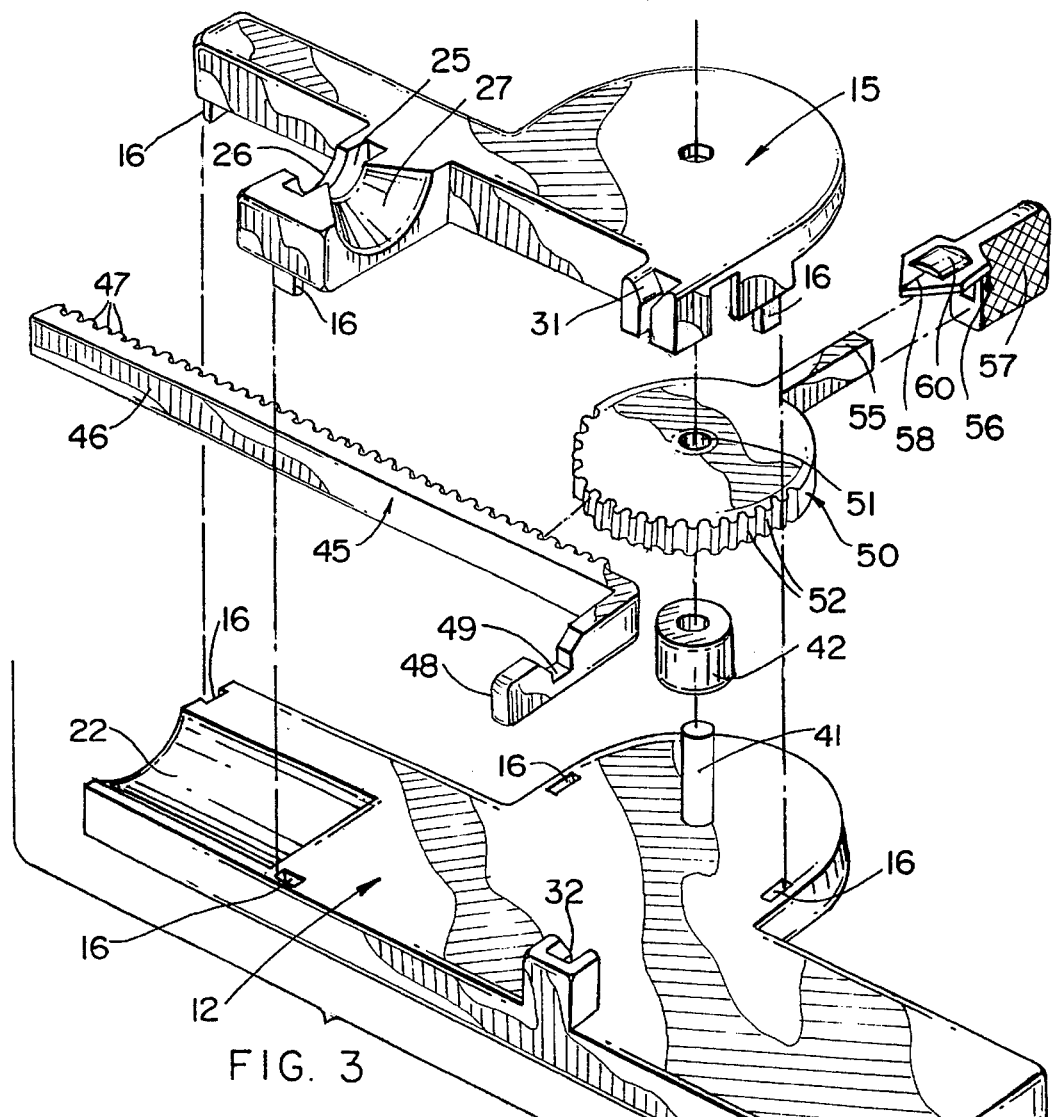
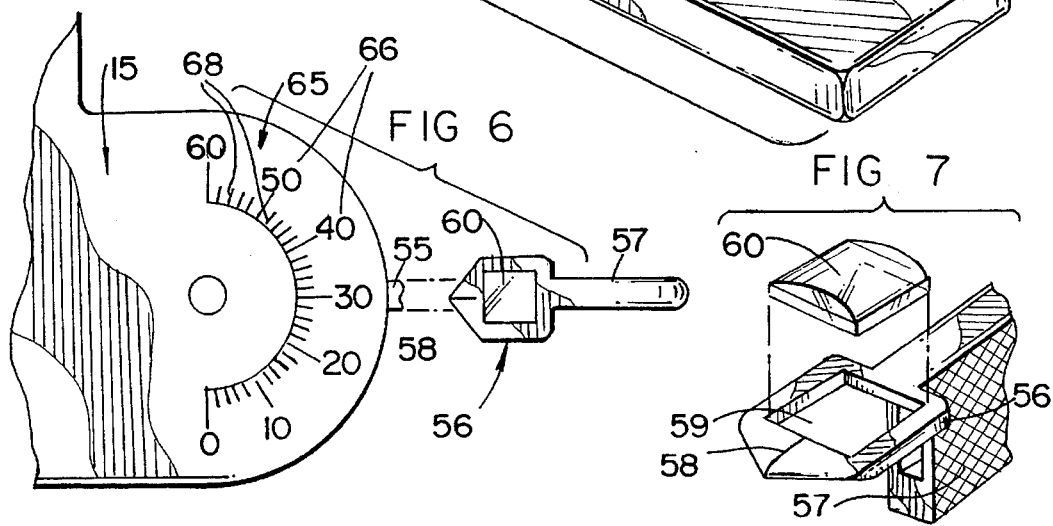

HYPODERMIC DOSAGE MEASURING DEVICE

BACKGROUND OF THE INVENTION

1. Field of the Invention

The present invention relates to a hypodermic dosage measuring device adapted to enable accurate and facilitated measurement of precise doses of a drug to be administered by means of a hypodermic syringe.

2. Description of the Related Art

Hypodermic syringes are a widely used method of dispensing needed drugs to individuals. They are utilized by doctors, nurses, as well as patients and other lay persons in a variety of circumstances. In addition to the careful handling of the syringe, one of the most important responsibilities undertaken by an individual dispensing a drug utilizing a syringe is to assure that the appropriate dosage is administered. Because hypodermic syringes generally administer the drug directly in the bloodstream or in the tissue of the patient, the dosage quickly and directly affects the patient. As a result, it is very important to assure that the precise dosage is administered at all times.

Commonly, hypodermic syringes which come in standard sizes include a gradated scale disposed on the body of the syringe. Utilizing the scale, an individual administering the drug will draw a quantity of the drug from a vial into the syringe, and then expel quantities of the drug until the precise dosage is achieved. This common measurement procedure can often be difficult and time-consuming, and most importantly can be quite wasteful as a quantity of the drug is expelled in order to achieve the appropriate dosage. Further, individuals who are self-administering a drug often suffer from ailments that affect their eyesight or coordination, thereby making it difficult to use the scale effectively. Because the scale is placed along a length of the syringe, the size of the numbers and scale is limited by the dimensions of the syringe such that larger, more easily read numbers cannot be implemented. As to the amount of the drug expelled, although it is seemingly small, due to the often expensive price of medication, even small amounts wasted over time can become quite costly.

In the past, there have been numerous devices adapted specifically for facilitating the measurement of the dosage drawn into a hypodermic syringe. These inventions include those disclosed in the references to Dobbins, U.S. Pat. No. 3,907,009, Ethington, U.S. Pat. No. 4,018,223, Right, U.S. Pat. No. 4,219,055, Maki, U.S. Pat. No. 4,252,159, LaDow, U.S. Pat. No. 4,778,454, and Bloom, et al., U.S. Pat. No. 4,098,276. The majority of these references, which were designed primarily to assist individuals such as diabetics in self-administering a medication, employ a common method of providing for a measured dosage. Particularly, the syringe is placed in the device and the plunger of the syringe is manually pulled by the individual until it arrives at a point on a scale or until it arrives at a stopper which will not let the plunger move any further. Such a means of measuring the dosage, however, has difficulties associated with its effective use. Principally, since the individual must manually pull the plunger or manipulate small inconveniently disposed buttons, sick or handicapped individuals may have difficulties in grasping the plunger in its location within the dose measuring device, or may not be able to provide a smooth, fluid pulling motion which could result in inaccurate measurement. Also, the measuring devices which do not require the user to judge the scale provide a set stopping location. The set stopping location is only effective if the same dosage must always be taken, because otherwise an individual, often a sick or handicapped individual, must manipulate the complicated adjustment means provided to adjust the positioning of the stopper. The complicated adjustment of the stopper not only defeats the purpose of making the device easy to use by sick or handicapped individuals, but also makes the device ineffective to utilize in a hospital setting where many different kinds of drugs requiring many different dosages must be used. Even in the case of patients administering their own drug, multiple drugs may need to be dispensed, and dosages may need to be varied depending on the condition of the individual.

Accordingly, it would be highly beneficial to provide a dosage measuring device which will hold the drug vial and the syringe in a convenient dispensing location where they may rest until the syringe is precisely needed, which pulls the plunger automatically as part of the dosage measuring means, and which provides a clear, easy to view indication of the precise dosage dispensed for a variety of drugs requiring a variety of dosages. The device of the present invention is designed specifically to meet these needs which remain in light of the related art.

SUMMARY OF THE INVENTION

The present invention is directed towards a hypodermic dosage measuring device. The dosage measuring device is adapted for use with a hypodermic syringe of the type including a needle, a dosage holding area, a flanged handle portion, and a plunger element slidably disposed within the dosage holding area. Further, the dosage measuring device is utilized with a conventional drug vial, the drug vial being of the type including a body to contain the drug, a neck, and a head portion through which the needle is inserted into the body of the vial for extracting the drug. The dose measuring device includes primarily a vial holding portion, a syringe holding portion, and a dose adjustment portion. The vial holding portion is specifically adapted to hold the head of the drug vial in a non-slidable position. The syringe holding portion, which is adapted to hold the hypodermic syringe in a drug extracting position, includes at least one channel member positioned to receive a side of the flanged handle portion of the syringe non-slidably therein. The channel member is spaced from the vial holding portion a sufficient distance such that the needle of the syringe is disposed within the vial when the vial is held in the vial holding portion and the handle portion of the syringe is held in the channel member. Included as part of the dose adjustment portion are an elongate, generally L-shaped plunger holder and a gear element. The plunger element has an elongated, toothed track segment adapted to slide in a longitudinal direction parallel to a length of the syringe. Extending perpendicularly from a proximal end of the toothed track segment is a plunger engagement segment. The plunger engagement segment is positioned to engage the plunger of the syringe such that longitudinal movement of the toothed track segment will result in corresponding longitudinal movement of the plunger. The longitudinal movement of the toothed track segment is controlled by the gear element. The gear element includes a plurality of teeth thereon and is positioned such that the teeth on the gear element engage the teeth on the track segment. Accordingly, movement of the gear element translates into corresponding movement of the track element. In order to facilitate movement of the gear element, handle means are included which are adapted to be held by a user when moving the gear element to measure a dose. Finally, in order to enable the amount of the drug dispensed to be precisely measured, dosage indicating indicia are included. The dosage indicating indicia are positioned such that an amount of the drug drawn into the syringe is indicated based on the position of the handle means relative to the indicia.

The object of the present invention is to provide a hypodermic dosage measuring device which will enable fast and consistently accurate measurement of precise doses of a drug to be dispensed by means of a syringe.

Another object of the present invention is to provide a hypodermic dosage measuring device which will enable sick, handicapped, and vision impaired individuals to quickly and easily measure out particular doses of a drug.

Yet another object of the present invention is to provide a hypodermic dosage measuring device which will ensure smooth and fluid motion of the plunger when drawing a drug into a syringe in a precise dosage.

A further object of the present invention is to provide a hypodermic dosage measuring device which will enable quick and facilitated measurement of varied dosages without requiring complex adaptation or adjustment of the device.

Yet another object of the present invention is to provide a hypodermic dosage measuring device which can maintain the drug vial and hypodermic syringe in a convenient, ready to use position before and after the dosage is dispensed.

Another object of the present invention is to provide a hypodermic dosage measuring device which will not necessitate that an individual dispensing the specific dosage manually manipulate the plunger in order to pull it a desired amount.

Still another object of the present invention is to provide a hypodermic dosage measuring device which will minimize waste by eliminating the need to draw a quantity more than the dosage amount and later eliminate quantities until the dosage amount is reached.

Also an object of the present invention is to provide a dosage measuring device which due to the radial movement of an adjustment handle, will not be limited to a specific size and spacing of the indicia and scale, but rather can accommodate larger sized indicia by placing the scale further radially outward.

BRIEF DESCRIPTION OF THE DRAWINGS

For a fuller understanding of the nature of the present invention, reference should be had to the following detailed description taken in connection with the accompanying drawings in which:

FIG. 1 is a perspective view of the dosage measuring device illustrating the positioning of the drug vial and hypodermic syringe therein.

FIG. 2 is a cross section view of the dosage measuring device along line 2—2 of FIG. 1.

FIG. 3 is an exploded perspective view of the dosage measuring device.

FIG. 4 is a cross-section view along line 4—4 of FIG. 1.

FIG. 5 is a cross-section view along line 5—5 of FIG. 1.

FIG. 6 is a top plan view of the dosage adjustment portion illustrating the relation between the dosage indicating indicia and the indicator means.

FIG. 7 is an isolated, exploded view of the indicator means of the present invention.

FIG. 8 is a perspective view illustrating the functioning of the dosage measuring device of the present invention.

FIG. 9 is a rear view of the dosage measuring device showing an alternative embodiment.

Like reference numerals refer to like parts throughout the several views of the drawings.

DETAILED DESCRIPTION OF THE PREFERRED EMBODIMENT

Shown throughout FIGS. 1–9, the present invention is directed towards a hypodermic dosage measuring device, generally indicated as 10. The dosage measuring device 10 is adapted for use with a hypodermic syringe 110 of the type which includes a needle 111, a dosage holding area 112, a flanged handle portion 114, and a plunger element 116 which is slidably disposed within the dosage holding area 112. Specifically, standard hypodermic syringes 110 generally come in a finite number of sizes, a dispensing facility commonly utilizing the same size syringe 110 for a majority of its drug administrations. Further, the dosage measuring device 10 is adapted for use with a conventional drug vial 100. The drug vial 100 is preferably of the type having a body 101, which is usually rounded in configuration, a narrow neck 102, and a head portion 104 through which the needle 111 of the hypodermic syringe 110 is inserted into the body 101 in order to extract a dosage of a desired drug.

The hypodermic dosage measuring device 10, which is formed principally of a base 12 and an upper molded housing 15 includes primarily a vial holding portion 20, a syringe holding portion 30, and a dose adjustment portion 40. The vial holding portion 20 is adapted to hold the drug vial 100 non-slidably therein and in a preferred embodiment includes a recess 22 formed in the base 12 which is adapted to receive the body 101 of the drug vial thereon. Further, the vial holding portion 20 includes a molded collar 25, preferably, formed in the upper housing 15. The molded collar 25 is adapted to receive the head 104 of the drug vial 100 therein and includes a curved neck restraining area 26 whereover the neck 102 of the drug vial 100 fits. With the neck 102 held in place, the body 101 of the drug vial 100 extends towards the distal end of the base 12 and rest in the recess 22. Extending from a proximal side of the molded collar 25 is a molded guide area 27 adapted to enable facilitated positioning of the needle 111 of the hypodermic syringe 110 into the drug vial 100 through a center of the head 104.

Included as part of the syringe holding portion 30 is at least one channel member 31, but in the preferred embodiment, there are a pair of spaced channel members 31 and 32. A first of the channel members 31 is preferably molded as part of the housing 15, and a second of the channel members 32 is preferably molded as part of the base 12. The channel members 31 and 32 are spaced and positioned to receive the opposite sides of the flanged handle portion 114 of the syringe 110 therein. Further, the channel members 31 and 32 are positioned such that the syringe 110 will be held in a non-sliding position atop the hypodermic dosage measuring device 10 while the needle 111 of the syringe 110 extends through the head 104 of the drug vial 100 and into the body 101 of the drug vial 100 so as to extract a quantity of the drug therefrom. The particular size and spacing of the spaced channel members 31 and 32 relate to a standard hypodermic syringe 110 design. As there are a finite number of hypodermic syringe designs, and a single facility generally uses the same design hypodermic syringe for all of its uses, the channel members 31 and 32 are moldable in only a small number of differing orientations.

Turning to the dosage adjustment portion 40, it includes primarily an elongate, generally L-shaped plunger holder 45 and a gear element 50, both of which are adapted to be substantially contained between the upper molded housing 15 and the base 12. Specifically, the upper molded housing 15 is adapted to be secured to one another. Preferably, they are snap-fitted by means of a plurality of pegs and apertures 16 atop the base 12 however, any securing means such as glues and the like are also contemplated. The L-shaped plunger holder 45 includes an elongate track segment 46 having a plurality of teeth 47 thereon. The track segment 45 is disposed between the housing 15 and base 12 such that the teeth 47 confront the gear element 50 of the dose adjustment portion 40, and such that it will slide longitudinally, in a direction parallel to a length of the syringe 110. Further, a proximal end of the toothed track segment 46 is adapted to protrude from beneath the molded housing 15 upon a longitudinal sliding thereof. The plunger holder 45 also includes a plunger engagement segment 48 which extends perpendicularly from the proximal end of the track segment 46. This plunger engagement segment 48 remains exterior of the molded housing 15 and slides along the base 12 so as to move the plunger 116 of the syringe 110. The engagement segment 48 includes a collar portion 49, the collar portion 49 preferably including a channel adapted to receive a lip 117 of the plunger 116 therein. In the preferred embodiment, the lip 117 rests directly in the channel of the collar 49 such that longitudinal movement of the track segment 46 in either direction will result in corresponding longitudinal movement of the engagement segment 48, and accordingly movement of the plunger 116. Such positioning enables movement in both directions such that if too much of the drug is extracted, it can be returned to the vial. In an alternative embodiment, the collar 49 abuts the lip 117 of the plunger 116 such that only outward movement of the plunger 116 relative to the dosage holding area 112 is achieved. Further positioned between the base 12 and the housing 15 is the gear element 50. The gear element 50 is preferably round and includes a plurality of teeth 52 along the peripheral edge thereof which are adapted to engage the teeth 47 along the track segment 46. The gear element 50 is adapted to rotate about a central axis defined by an axis post 41 which preferably extends upwardly from the base 12. Preferably, a washer element 42 is first disposed over the axis post 41 to facilitate rotation of the gear element 50 which is disposed over the axis post 41 through a central opening 51. Extending from the gear element 50 is an elongate handle segment 55. The handle segment 55 is disposed so as to protrude from between the base 12 and molded housing 15 and facilitate actuation by a user. By sliding the elongate handle segment 55, the gear element 50 rotates resulting in corresponding longitudinal movement of the plunger holder 45.

As seen in FIG. 6, positioned on an exterior surface of the molded housing 15, directly over the location of the gear element 50, are dosage indicating indicia 65. The dosage indicating indicia 65 may include a numbered scale 66, a gradated line scale 68, or a combination of both. The dosage indicating indicia 65 is specifically positioned so as to indicate an amount of the drug drawn into the syringe 110 from the drug vial 100, the amount being based on the position of the handle element 55 relative to the indicia 65. Also, because of the round configuration of the gear element 50 and the radial orientation of the handle segment 55, the indicia 65 can be made substantially larger merely by extending the handle segment 55 and increasing the size of the housing 15. In this manner, the size of the indicia is not limited by the size of the syringe 110. So as to further facilitate precise indication of the dosage drawn into the syringe 110, indicator means 56 are included over the handle segment 55. Particularly, the indicator means 56 include a gripper area 57 adapted to be positioned over the end of the handle segment 55 to facilitate grasping of the handle segment 55 by a user. Extending over the handle segment 55, as part of the indicator means 56, is a pointer 58. The pointer 58 is adapted to be positioned directly on the molded housing 15 over the indicia 65 such that the point 58 indicates a precise dosage amount as indicated on the gradated line scale 68. In order to further assist viewing of the precise dosage, particularly for those individuals with impaired vision, the indicator means 56 includes a window opening 59 wherein a magnifying lens 60 can be positioned. This forms a magnified viewing slot adapted to pass directly over the numbered scale 66 of the dosage indicating indicia 65, thereby making the numerals easier to read and improving the ability of a user to determine the precise dosage amount. Accordingly, merely by sliding the handle segment 55 from its starting point with the indicator means 56 indicating zero dosage, a precise dosage will be drawn into the syringe 110, the precise dosage amount being limited only by the needs of the patient and not by a fixed stopper which only enables one dosage to be measured by the device.

In order to facilitate use in the hospital or like location, a dosage measuring device 10 can be adapted to be wall mounted, thereby making it convenient for frequent uses. In order to achieve this, the dosage measuring device 10 can include wall mounting means. Preferably, the wall mounting means are in the form of a pair of apertures 14 disposed in a rear surface 13 of the base 12, the openings 14 being adapted to receive a screw or nail, which has been secured to a wall, therein.

Now that the invention has been described,

What is claimed is:

1. A hypodermic dosage measuring device to be utilized with a hypodermic syringe of the type including a needle, a dosage holding area, a flanged handle portion, and a plunger element slidably disposed therein, and a conventional drug vial having a body, a neck, and a head portion through which the needle is inserted into the body of the vial; said hypodermic dosage measuring device comprising:

a vial holding portion connected to a syringe holding portion by a dose adjustment portion;

said vial holding portion comprising a recess adapted to hold the head of the drug vial non-slidably therein, said syringe holding portion including at least one channel member for receiving a side of the flanged handle portion of the syringe non-slidably therein, and being sufficiently spaced from said vial holding portion such that the needle of the syringe is disposed within the vial upon the vial being positioned in said vial holding portion and the handle portion of the syringe being positioned in said channel member;

said dosage adjustment portion including an elongate, generally L-shaped plunger holder;

said plunger holder including an elongate, toothed track segment slidable in a longitudinal direction parallel to a length of the syringe, said plunger holder further including a plunger engagement segment extending perpendicular from a proximal end of said toothed track segment so as to engage the plunger such that longitudinal movement of said track segment results in corresponding longitudinal movement of the plunger of the syringe, said dosage adjustment portion further including a gear element, said gear element including a plurality of teeth thereon such that movement of said gear element results in corresponding movement of said track segment, handle means extending from and fixed to said gear element to facilitate movement of said gear element, and dosage indicating indicia on said measuring device to visually indicate an amount of drug drawn into the syringe based on the position of said handle means relative to said dosage indicating indicia, wherein a position of said handle means relative to said indicating indicia visually indicates a relative position of said plunger engagement segment with respect to said vial holding portion.

2. A dosage measuring device as recited in claim 1 further including a base and an upper molded housing, said housing secured atop said base to contain said gear element and said toothed track segment of said plunger holder movably between said housing and said base.

3. A hypodermic dosage measuring device as recited in claim 2 wherein said gear element rotates about a centrally disposed axis post extending from said base.

4. A hypodermic dosage measuring device as recited in claim 3 wherein said handle means of said gear element includes an elongate handle segment integrally formed with said gear element and protruding from said gear element through said housing so as to facilitate rotation of said gear element, said handle segment being radially disposed relative to said axis post, and said dosage indicating indicia being positioned adjacent a distal end of said handle segment such that increasing a length of said handle segment will facilitate increasing a size of said dosage indicating indicia.

5. A hypodermic dosage measuring device as recited in claim 4 further including indicator means on said elongate segment of said handle means so as to indicate an exact position of said handle means relative to said dosage indicating indicia, said dosage indicating indicia being disposed on an exterior surface of said housing.

6. A hypodermic dosage measuring device as recited in claim 5 wherein said indicator means includes a magnified viewing slot to magnify said dosage indicating indicia disposed beneath said indicator means.

7. A hypodermic dosage measuring device as recited in claim 6 wherein said base includes wall mounting means to enable said base and said housing to be mounted in a vertical orientation to a wall surface.

8. A hypodermic dosage measuring device as recited in claim 1 including a pair of said channel members disposed in spaced apart relation from one another so as to hold opposite sides of the handle portion of the syringe.

9. A hypodermic dosage measuring device as recited in claim 8 wherein said vial holding portion includes a molded collar to hold the head of the vial therein and enable the neck of the vial to pass therethrough towards a distal end of said base.

10. A hypodermic dosage measuring device as recited in claim 9 wherein said engagement segment includes a channel to receive a lip of the plunger therein.

11. A hypodermic dosage measuring device as recited in claim 10 wherein said vial holding portion includes a recess in said base, for receiving the body of the vial supportably therein.

* * * * *